United States Patent [19]

Hubbard et al.

[11] Patent Number: 4,571,245
[45] Date of Patent: Feb. 18, 1986

[54] PERSONAL CATHETER LEG STRAP

[75] Inventors: Vance M. Hubbard, Euless; Welton K. Brunson, Bedford, both of Tex.

[73] Assignee: Tecnol, Inc., Fort Worth, Tex.

[21] Appl. No.: 479,671

[22] Filed: Mar. 28, 1983

[51] Int. Cl.⁴ .......................................... A61M 25/02
[52] U.S. Cl. ........................... 604/179; 128/DIG. 26
[58] Field of Search ........................ 604/174, 179–180; 128/DIG. 26

[56] References Cited

U.S. PATENT DOCUMENTS

| | | | |
|---|---|---|---|
| 3,430,300 | 3/1969 | Doan | 604/180 X |
| 4,088,136 | 5/1978 | Hasslinger et al. | 604/179 |
| 4,096,863 | 6/1978 | Kaplan et al. | 604/179 |
| 4,445,894 | 5/1984 | Kovacs | 604/179 |

*Primary Examiner*—Dalton L. Truluck
*Attorney, Agent, or Firm*—Jerry W. Mills; Gregory M. Howison

[57] ABSTRACT

A catheter tube holder (10) includes a first section (12) of a gauze type material and a second section (14) of elastic type material joined together at a seam (16) for wrapping about a limb. A Velcro-type strip (30) attaches the two free ends together. A securing strap (22) is attached at one end thereof to the seam (16) and has two portions (24) and (26), of which the portion (26) is narrower. An orifice (28) is disposed in the broad portion (24) and is dimensioned such that the narrow portion (26) is insertable therein. The securing strap (22) has a free end thereof wrapped about a catheter tube (32) and inserted through the orifice (28) after wrapping about the tube (32) one revolution. The strap (22) is then wrapped an additional one-half revolution about the catheter tube (32) and attached to the surface (20) with a Velcro-type fastener.

1 Claim, 4 Drawing Figures

PERSONAL CATHETER LEG STRAP

TECHNICAL FIELD

The invention pertains in general to tubular securing devices and, more particularly, to a device for securing a catheter tube on a portion of the anatomy adjacent the catheter insertion point.

BACKGROUND OF THE INVENTION

Catheter securing devices provide a very useful function in immobilizing the catheter tube after insertion of the catheter. Normally these devices secure the catheter to a limb in close proximity to the insertion point of the catheter to provide an immobilizing function to enable a patient some additional degree of mobility with the catheter inserted. In addition to the immobilizing function, the catheter securing device also must provide a certain degree of comfort to the patients since these devices are normally attached for some length of time.

An example of a catheter securing device is disclosed in U.S. Pat. No. 4,096,863 issued to Kaplan et al. The Kaplan device illustrates a strap that is operable to be secured around the limb and having a secondary strap attached thereto for wrapping about the catheter tube. The secondary strap has a Velcro-type material attached thereto for mating with a second Velcro-type material disposed on the surface of the primary strap wrapped about the limb. The secondary strap wraps about the catheter tube and loops back through a metal ring. This metal ring allows the secondary strap to be tightened around the catheter over a large portion of the circumference thereof. However, a portion of the catheter tube is disposed adjacent the opening of the metal ring thereby exhibiting a tendency to "pinch" the catheter tube. As the secondary strap is tightened around the catheter tube, the catheter tube tends to bulge through the metal ring thereby increasing the pinching effect.

In view of the prior art, there exists a need for a catheter tube securing apparatus that firmly holds the catheter tube in place with uniform restriction about the entire circumference of the tube.

SUMMARY OF THE INVENTION

The present invention disclosed and claimed herein comprises an apparatus for securing a tubular device. The apparatus includes a first resilient strip for providing a mounting surface with a fastening material attached to one end for fastening to the other end thereof for attaching the first resilient strip to a selected area where the tubular device is to be secured. A second resilient strip is attached at one end thereof to the first resilient strip. The second resilient strip has a first portion with the first width and a second portion with a second and wider width. The second portion is adjacent the first resilient strip and has an orifice disposed through the surface thereof dimensioned to receive the first portion. The free end of the first portion is operable to wrap around the tubular device at least one revolution and insert through the orifice in the second portion. The free end is then wrapped essentially an additional one-half revolution about the tube and attached to the surface of the first resilient strip.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
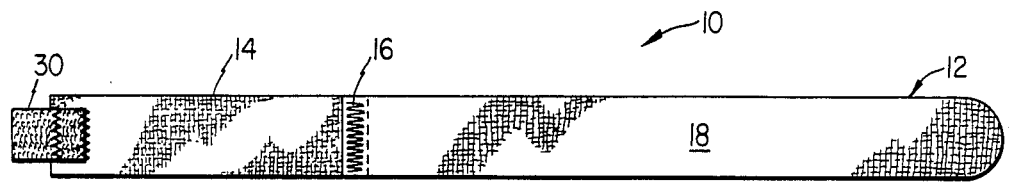
FIG. 1 is a plan view of the inner surface of the catheter tube securing device.
Figure 2:
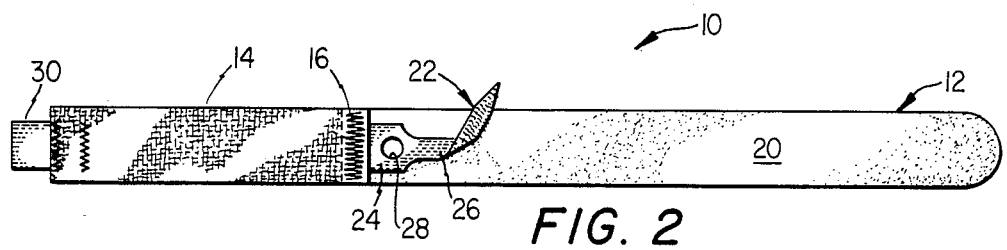
FIG. 2 illustrates a plan view of the outer surface of the catheter tube securing device.

Referring now to FIGS. 1 and 2, there are illustrated plan views of both sides of a catheter tube holder 10. The tube holder 10 is divided into two sections 12 and 14 that are attached together at one end thereof by a seam 16. The section 14 is fabricated of an elastic webbing material which is stretchable in a lengthwise direction but has a relatively defined dimension across its width. The section 12 is fabricated of a gauze type material having a woven surface 18 on the bottom side thereof, as depicted in FIG. 1, and a fibrous surface 20 on the top side thereof, as depicted in FIG. 2. This fibrous surface can be a cotton or similar type material.

A securing strap 22 is attached at one end thereof to the seam 16 and oriented such that it lays essentially parallel to the surface 20 of the section 12. The securing strap 22 is divided into a broad portion 24 and a narrow portion 26, the broad portion 24 being disposed adjacent the seam 16. The broad portion 24 of the securing strap 22 has an orifice 28 with a diameter essentially equal to or slightly larger than the width of the narrow portion 26. As will be described hereinbelow, the narrow portion 26 is dimensioned to insert into the orifice 28. It should be understood that, although the orifice 28 is shown as a circle, it can be configured in any number of ways. For example, one configuration of the orifice could be a slot that is parallel to the seam 16.

The surface of the securing strap facing the surface 20 of the section 12 has a plurality of small hooklike elements disposed thereon to provide a Velcro-type material. The small hooklike elements are operable to mate with the fibrous material of the surface 20 to interconnect thereto. This type of fastening device allows the securing strap 22 to be firmly fastened to the surface 20 of the section 12. "Velcro" is a trademark for an attachment device having small hook shaped members on one surface and loose fibers on a mating surface. When these two surfaces are joined, the hook shaped members "tangle" with the fibrous material to form a bond therebetween which is easily separable.

A Velcro-type strip 30 is attached to the end of the section 14 diametrically opposite the seam 16. The Velcro-type strip 30 has a plurality of hooklike elements disposed on one surface thereof and oriented such that they mate or interlock with the fibrous material of the surface 20 when the end of the section 14 is wrapped around a limb or other such surface to meet with the end of the section 12.

Figure 3:
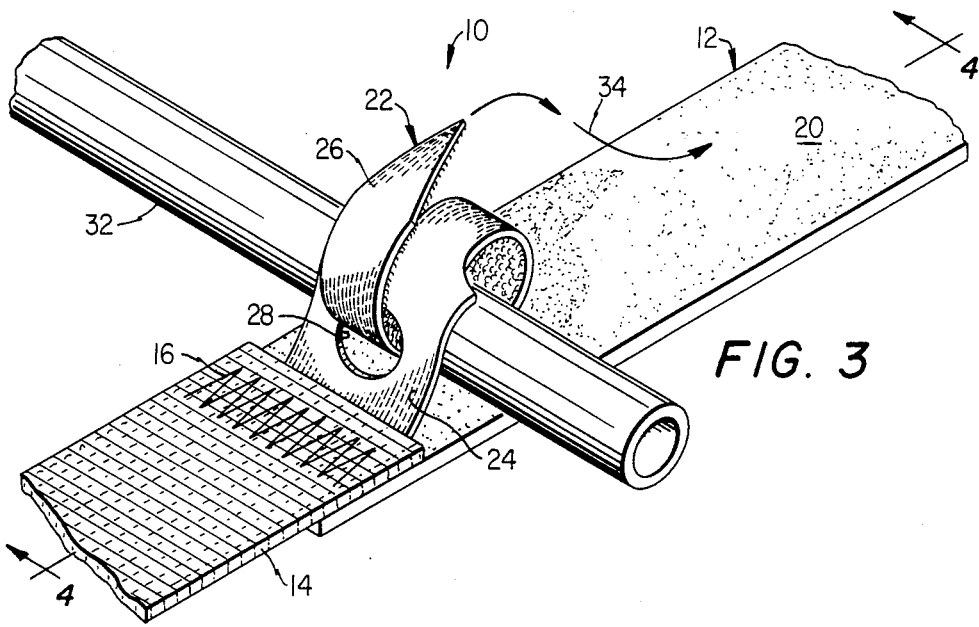
FIG. 3 illustrates a perspective view of the catheter securing device with the catheter tube in place.

Referring now to FIG. 3, there is illustrated a perspective view of the catheter tube holder 10 with the securing strap 22 loosely wrapped about a catheter tube 32. To secure the catheter tube 32, the tube 32 is placed between the under side of the securing strap 22 and also between the strap 22 and the surface 20. The free end of the securing strap 22 is then wrapped about the tube 32 and inserted through the orifice 28. This effectively results in one revolution of the securing strap 22 around the tube 32. The free end of the securing strap 22 is then wrapped an additional onehalf revolution around the tube 32 in the direction of arrows 34 for attachment to the surface 20.

Figure 4:
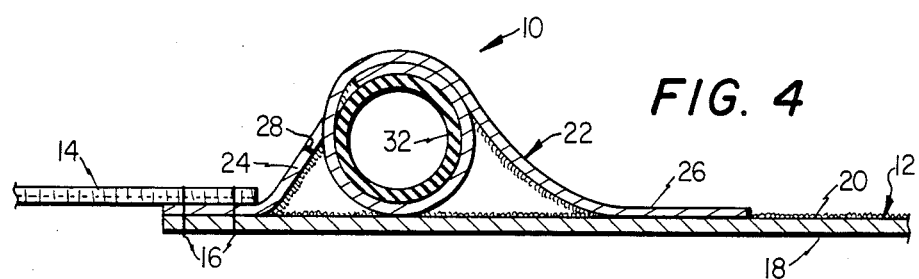
FIG. 4 illustrates a cross sectional view of the device in FIG. 3 taken along line 4—4 thereof.

The secured position of the securing strap 22 about the tube 32 is better illustrated in the cross sectional view in FIG. 4 taken along lines 4—4 of FIG. 3. As illustrated, the tube 32 is secured by the securing strap 22 wrapped thereabout approximately one and one-half revolutions and attached at the free end thereof to the fibrous material on the surface 20. It is important to note that the securing strap 22 is wrapped about the tube 32 in such a manner that there is resulting downward force on the tube directed toward the surface 20. This, in combination with the one and onehalf revolutions around the tube, adequately secures the tube 32 against the surface 20. The circumventing of the tube 32 is an important aspect of the present invention in that "pinching" of the tube 32 is prevented. This pinching can result in constriction of the tube through the secured portion. By circumventing the tube, it is not possible to constrict the passage therethrough without substantially deforming the tube 32. However, if the forces are unevenly distributed, the tube 32 exhibits a tendency to take on an oblique shape. By spreading the forces evenly, this is prevented.

In summary, there has been provided a catheter tube holder that includes a strap formed of an elastic portion and a fibrous portion that is held together around a limb by a Velcro fastener. A securing strap attached at one end thereof to the junction of these two sections and dimensioned to have the free end thereof of a narrower width than the attached end. The free end is operable to wrap around the catheter tube one revolution and insert through an orifice in the wider section of the securing strap. The free end of the securing strap is then wrapped an additional one-half revolution about the catheter tube and attached to the surface of the fibrous section with a Velcro-type fastener. The securing strap is wrapped about the catheter tube in such a manner to cause a resulting downward force on the catheter tube to thereby hold it firmly against the surface of the strap.

Although the preferred embodiment has been described in detail, it should be understood that various changes, substitutions and alterations can be made therein without departing from the spirit and scope of the invention as defined by the appended claims.

What is claimed is:

1. An apparatus for securing a catheter tube to a portion of the anatomy of a patient adjacent a catheter insertion point, comprising:

a strap for wrapping about the desired portion of the anatomy of the patient, said strap having a first elastic portion for stretching and a second portion having a layer of fibrous material disposed on one side for receiving Velcro-type attaching layer, said first portion having a length roughly similar to the length of said second portion, said first and second portions each having an end joined to each other at a junction, said first and second portions each having a free end;

a strip of Velcro-type material attached to the free end of said first portion for mating with the free end of said second portion, said second portion having the fibrous material thereon to form an attachment therebetween;

a securing band having Velcro-type hook members disposed on one side thereof, said securing band attached at said junction between the first and second portions thereof to lie parallel and over the second portion, when not in use so that said hook members face downward, said securing band including a first portion having a circular orifice disposed therethrough adjacent the attached end and a second portion integrally attached to said first portion proximate the orifice, the width of said second portion being less than the width of said first portion and also the width of said first portion being less than the width of said strap, the width of said second portion being less than the diameter of said orifice through the entire length of said second portion, said second portion having a pointed free end for insertion through said orifice;

said securing band operable to wrap around the catheter tube one revolution for insertion of said second portion through said orifice and further wrap around the catheter tube essentially one-half revolution for attachment of the Velcro-type hook members on the surface of said securing band to the fibrous material on the surface of said strap at any of a plurality of locations such that said catheter tube is secured against the surface of said strap vertically and laterally by said securing band providing a downward force on the catheter tube directed toward the strap, whereby any one of a plurality of catheter tubes having different diameters may be comfortably and securely attached to the patient's leg.

* * * * *